(12) United States Patent
Walker

(10) Patent No.: US 9,931,215 B2
(45) Date of Patent: Apr. 3, 2018

(54) TOTAL KNEE REPLACEMENT IMPLANT BASED ON NORMAL ANATOMY AND KINEMATICS

(75) Inventor: Peter Stanley Walker, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/877,541

(22) PCT Filed: Oct. 11, 2011

(86) PCT No.: PCT/US2011/055764
§ 371 (c)(1),
(2), (4) Date: Apr. 3, 2013

(87) PCT Pub. No.: WO2012/051178
PCT Pub. Date: Apr. 19, 2012

(65) Prior Publication Data
US 2013/0204382 A1    Aug. 8, 2013

Related U.S. Application Data

(60) Provisional application No. 61/392,172, filed on Oct. 12, 2010, provisional application No. 61/454,023, filed on Mar. 18, 2011.

(51) Int. Cl.
*A61F 2/38* (2006.01)
*A61F 2/30* (2006.01)

(52) U.S. Cl.
CPC .............. *A61F 2/38* (2013.01); *A61F 2/3886* (2013.01); *A61F 2002/30948* (2013.01); *A61F 2002/30952* (2013.01)

(58) Field of Classification Search
CPC ...... A61F 2/30942; A61F 2/38; A61F 2/3836; A61F 2/385; A61F 2/3859; A61F 2002/3863; A61F 2/3868
USPC ......... 623/20.31, 20.21, 20.14, 20.15, 20.18, 623/20.27, 20.35
See application file for complete search history.

(56) References Cited

U.S. PATENT DOCUMENTS

| | | | |
|---|---|---|---|
| 6,699,291 B1 * | 3/2004 | Augoyard et al. | 623/20.27 |
| 6,712,856 B1 * | 3/2004 | Carignan et al. | 623/20.35 |
| 2004/0243244 A1 * | 12/2004 | Otto et al. | 623/20.27 |
| 2007/0135925 A1 | 6/2007 | Walker et al. | |

(Continued)

OTHER PUBLICATIONS

Angelo, Rita di Cassia de Oliveira. Morphometric study of the femoral intercondylar notch of knees with and without injuries of the ACL by the use of software in digitalized radiographic images. Acta Orthopedica Brasileira. 12(3) Jul. 2004.*

(Continued)

*Primary Examiner* — Christopher D Prone
(74) *Attorney, Agent, or Firm* — Kilpatrick, Townsend & Stockton, LLP

(57) ABSTRACT

A total knee replacement prosthesis is presented whose bearing surfaces are derived from an anatomically representative femur and a modified baseline tibial surface. The contacting femoral and tibial bearing surfaces include the inter-condylar as well as condylar regions. The modified baseline tibial surface is generated by modifying a baseline tibial surface. For example, the baseline tibial surface can be flattened mathematically to generate the modified baseline tibial surface.

13 Claims, 6 Drawing Sheets

(56) References Cited

U.S. PATENT DOCUMENTS

| | | | |
|---|---|---|---|
| 2007/0135926 A1* | 6/2007 | Walker | 623/20.31 |
| 2009/0204221 A1 | 8/2009 | Walker | |
| 2009/0319047 A1* | 12/2009 | Walker | A61F 2/3886 |
| | | | 623/20.15 |
| 2009/0319049 A1* | 12/2009 | Shah et al. | 623/20.31 |
| 2012/0116524 A1 | 5/2012 | Walker et al. | |

OTHER PUBLICATIONS

PCT Preliminary Report on Patentability PCT/US2011/055764; dated Apr. 16, 2013.

\* cited by examiner

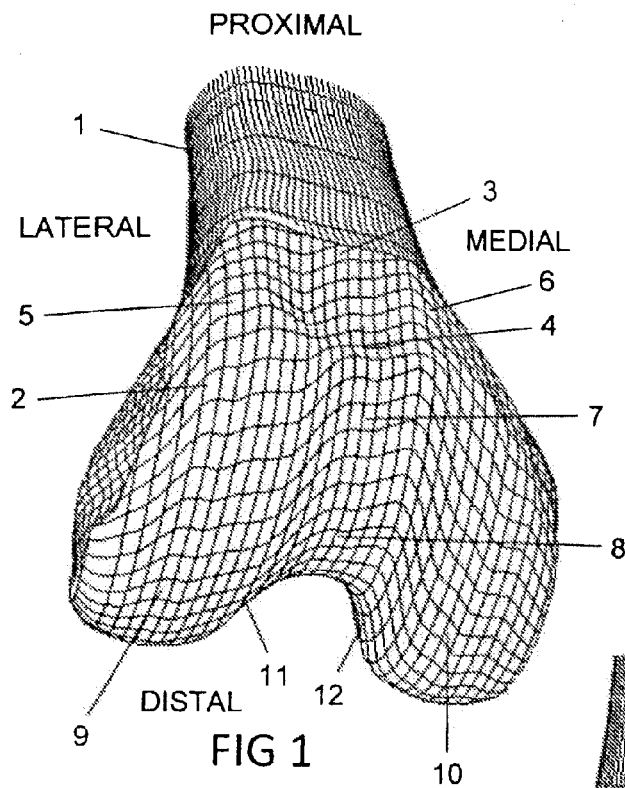
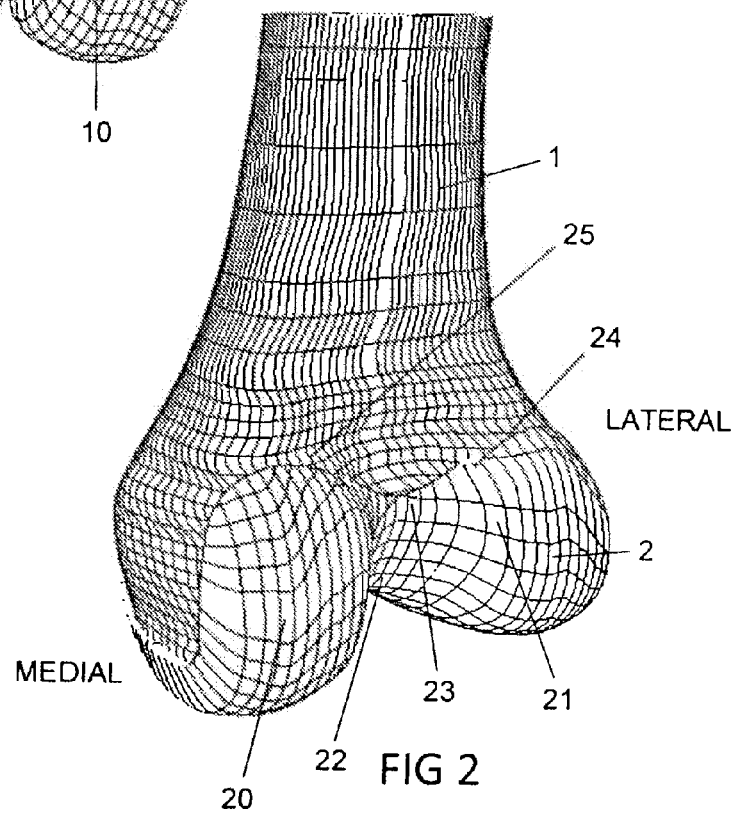

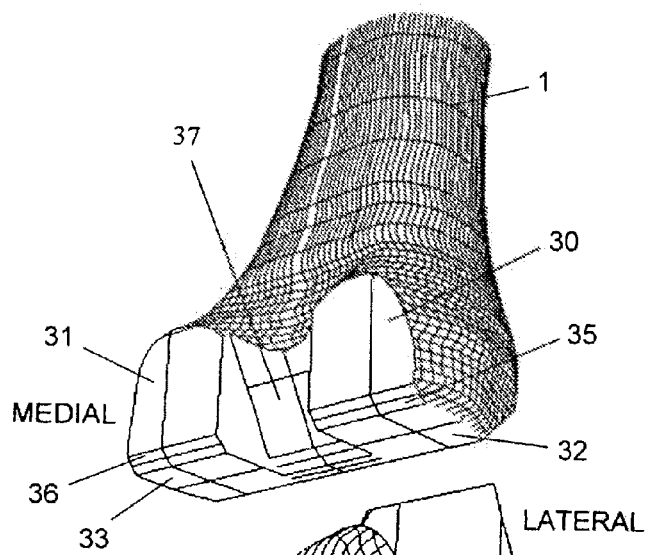
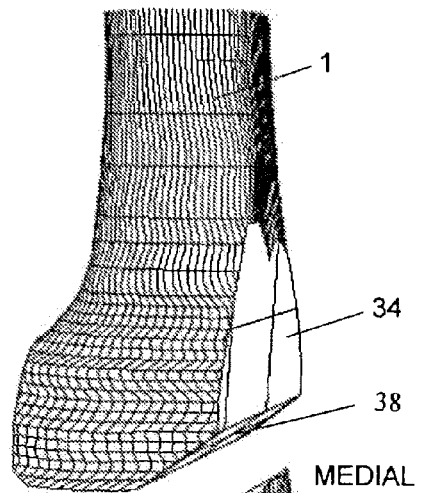
FIG 3
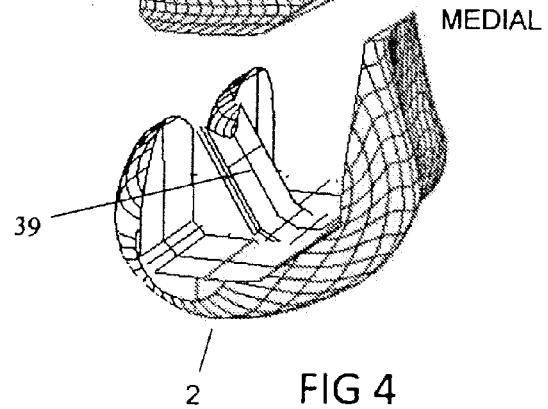
FIG 4

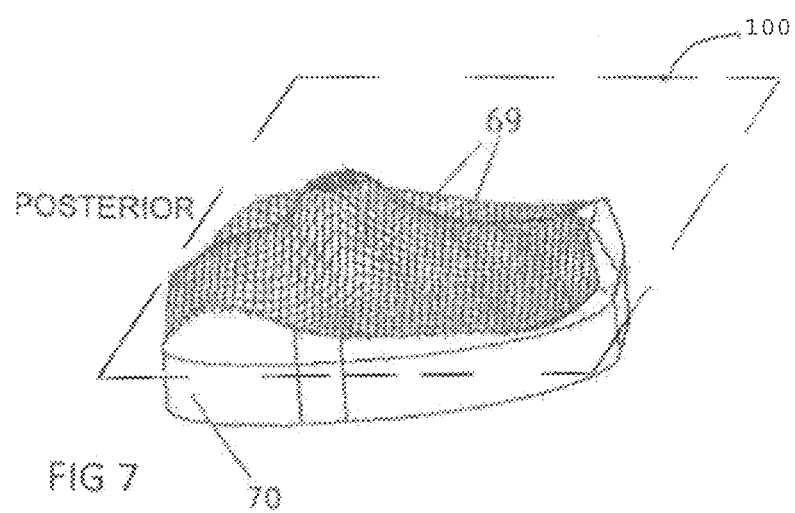
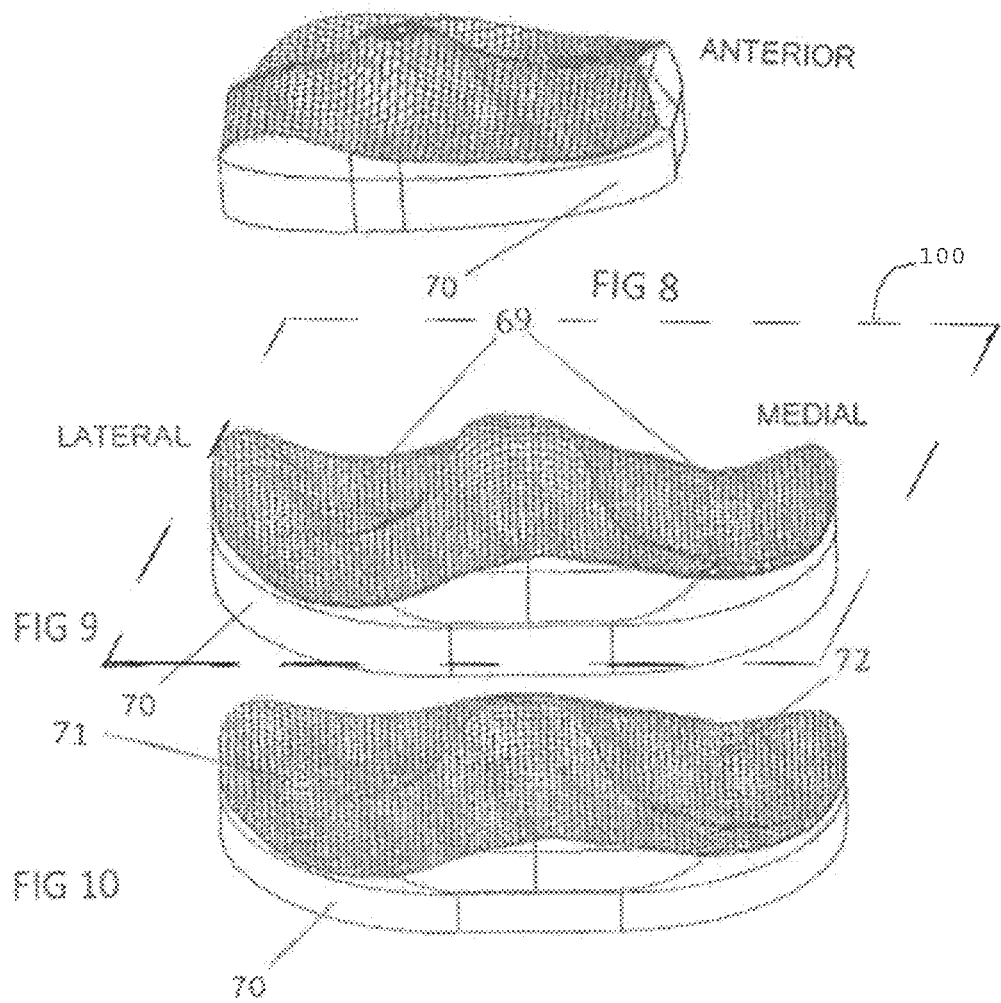

TOTAL KNEE REPLACEMENT IMPLANT BASED ON NORMAL ANATOMY AND KINEMATICS

PRIORITY CLAIM TO PREVIOUS PATENT APPLICATIONS

This non-provisional U.S. patent application, under 35 U.S.C. 371, claims the benefit of priority from PCT application, PCT/US11/55764, filed 11 Oct. 2011, that claims priority from U.S. Provisional Patent Application No. 61/392,172, filed 12 Oct. 2010, and U.S. Provisional Patent Application No. 61/454,023, filed 18 Mar. 2011, the entire disclosures of which are incorporated by reference in their entirety.

BACKGROUND OF THE INVENTION

Field of the Invention

The present invention generally relates to knee implant where the femoral component is derived directly from anatomic shapes, including the femoral trochlea, the lateral bearing surface, the medial bearing surface, and the intercondylar area between them.

Description of the Related Art

The first condylar replacement type of total knee replacement intended for cruciate resection was the Freeman-Swanson (Freeman, Swanson, Todd 1977), designed in the late 1960's. This used a roller-in-trough geometry to provide stability and a large area of contact to minimize the wear. Also in the late 1960's, Gunston (1971) designed a conservative total knee consisting of independent runners embedded in the femoral and tibial condyles. In the early 1970's, Seedhom (1974) designed a total knee based on anatomical knee specimens, where he directly replicated the femoral surfaces and the tibial surfaces with the menisci present. A similar concept was described by Ewald in a patent. The Total Condylar knee was designed in the early 1970's with partially conforming bearing surfaces in the frontal and sagittal planes In order to provide an appropriate combination of laxity and stability (Walker, Wang, Masse 1974; Insall, Ranawat, Scott, Walker 1976). The relative radii were calculated to provide similar mechanical characteristics to that of the anatomic knee. The Kinematic Stabilizer and Insall-Burstein designs added an intercondylar cam-post mechanism to prevent anterior femoral subluxation and posterior femoral displacement in high flexion (Walker & Sathasivam, 2000; Robinson RD 2005). Since then, these 'posterior stabilized' (PS) designs have been modified and refined, and are now in widespread use. Typically the sagittal and frontal geometrics are defined by connecting radii generally resembling the Total Condylar, while the intercondylar cam-post is designed separately, usually contacting from mid-flexion to maximum flexion. In such designs, the lateral and medial condyles are often symmetric, providing no lateral or medial bias to the motion. While symmetric designs can use simply derived geometry for both the femoral and tibial surfaces, as well as for cams and posts, such an approach is more difficult if anatomic motion patterns are required. For any type of design where both of the cruciates are resected, the problem of replicating the constraints provided by these ligaments remains a challenge to this day. In particular, providing AP stability and rotational laxity throughout flexion, while inducing femoral rollback to achieve high flexion angles without posterior impingement, seems difficult to achieve with the bearing surfaces alone, even with a cam-post mechanism.

A further drawback of standard designs is that they only approximate the anatomical geometry, such that the metallic and plastic components do not closely replicate the bone and cartilage shapes which are removed at surgery. This results in altered ligament length patterns and muscle lever arms, which can cause instability, tightness in certain parts of the flexion arc, or inefficient use of muscles, or even pain such as in the patello-femoral joint.

More recently, designs have been produced which provide greater medial than lateral constraint. One design concept, the medial pivot, uses a ball-in-a-socket for the medial compartment, and surfaces of low constraint on the lateral side (Blaha 2004; Moonot, 2009). Another design, the Journey Knee (Reis, Victor, Bellemans 2006, Victor Bellemans 2006), has a more constrained medial side and a cam-pivot which results in more posterior femoral displacement laterally. These designs are intended to achieve more normal kinematics, a goal that is receiving more attention today in an effort to improve function, especially in more active patients. So far however, these designs do not replicate anatomic motion and laxity-stability characteristics, or have certain motion abnormalities in some patients. Hence there is still a need for a design that will allow close restoration of normal kinematics, and provides reliability and reproducibility.

SUMMARY OF THE INVENTION

An artificial knee where the femoral component is presented that is derived directly from anatomic shapes, including the femoral trochlea, the lateral bearing surface, the medial bearing surface, and the intercondylar area between them. All of the bearing surfaces are smoothly connected. Certain dimensions and radii are specified as representing key dimensional parameters for the composite surface. The tibial component comprises a bearing surface that is generated from a multiplicity of femoral component positions that represent the average neutral path of knee motion and the laxity about the neutral path. Specified modifications are made to the anatomical motion to avoid excessive edge loading of the femoral component on the tibial component at the extremes of motion. An algorithm for modification of the multiple femoral components is shown, for the purpose of providing appropriate dishing and restraint of excessive motions. The tibial surface generated in the above manner would have a close fit with the femoral surface, which has the disadvantage of requiring extreme manufacturing tolerances, and would also promote edge loading for eccentric loading conditions. To alleviate these problems, an algorithm is shown for modifying the tibial surface to allow appropriate clearances with the femoral surface. One important feature of the tibial surface is a relief on the posterior medial side, which is an imprint of the posterior of the implant and of the posterior femoral condyles in high flexion. This provides clearance to facilitate such flexion and avoid impingement on the plastic. A further tibial feature is the central area which is generated by the intercondylar area of the femoral component. This raised hump on the tibial surface provides motion guidance and stability in multiple directions and at multiple positions in the flexion arc.

In embodiments there is disclosed a knee replacement implant comprising a femoral component comprising a distal femoral bearing surface having a medial condylar region, a lateral condylar region and an intercondylar region and being defined by a plurality of frontal profiles, each corresponding to an angle of flexure, each of the plurality of frontal profiles representing a projection, onto a coronal plane, of the distal profile of a baseline anatomically representative femur, each of the plurality of the frontal profiles of the distal femoral bearing surface comprises a convex medial condylar portion, tangentially and smoothly transitioning into a concave intercondylar portion, tangentially and smoothly transitioning into a convex lateral condylar portion, the intercondylar portion defined by an intercondylar radius, an intercondylar housing height, an intercondylar sidewall angle, a tibial component comprising a proximal tibial bearing surface, wherein the proximal tibial bearing surface is operatively configured to engage the distal femoral bearing surface throughout a full range of flexure angles, the proximal bearing surface being a modification from a baseline tibial surface, where the baseline tibial surface is defined as an envelope of the composite of the distal femoral bearing surfaces positioned, with respect to the tibial component, throughout the full range of flexure angles and axial rotation angles.

BRIEF DESCRIPTION OF DRAWINGS

The accompanying figures incorporated in and forming a part of the specification illustrate several aspects of embodiments of the invention and, together with the description, serve to explain the embodiments.

FIG. 1 is a distal-anterior view of the femoral component mounted on the distal femur.

FIG. 2 is a medial-posterior view of the femoral component mounted on the distal femur.

FIG. 3 is a distal-posterior view showing the femoral component (below) and the distal femur (above).

FIG. 4 is a lateral-anterior view showing the femoral component (below) and the distal femur (above).

FIG. 7 is a lateral view of the tibial component generated directly by the femoral component.

FIG. 8 is a lateral view of the tibial component where the vertical coordinates of the surface have been reduced by a factor of 0.7.

FIG. 9 is an anterior view of the tibial component generated directly by the femoral component.

FIG. 10 is an anterior view of the tibial component where the vertical coordinates of the surface have been reduced by a factor of 0.7.

DETAILED DESCRIPTION OF THE INVENTION

Figure 5:
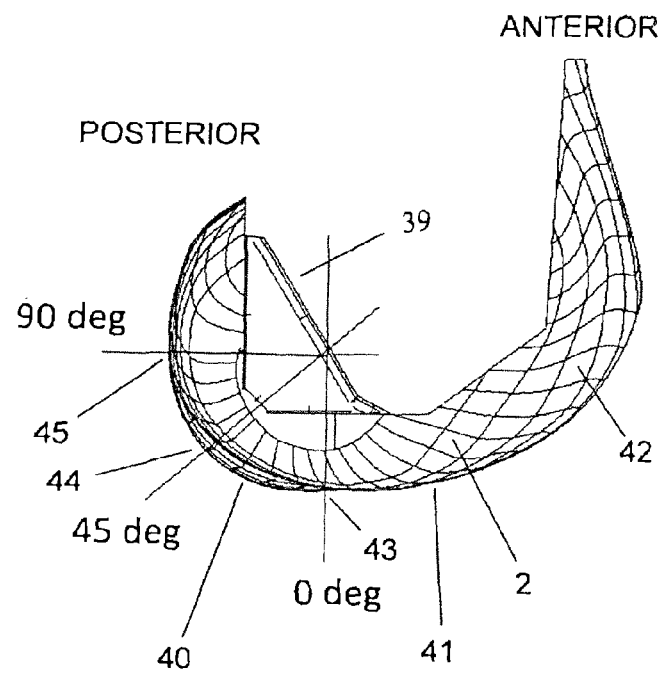
FIG. 5 is a lateral view of the femoral component.

In FIGS. 1 and 2, the distal femur 1 is shown with the femoral component 2 fixed in place. The outer bearing surface of the femoral component is a replica of the anatomic distal femur for the purpose of illustration, but this can be modified slightly for purposes of smoothing, making surfaces of definable geometrical parameters, or manufacturability.

A baseline anatomically representative femur is defined as a femoral prosthesis comprising a distal bearing surface that duplicates that of an anatomic femur. The distal bearing surface shape can be taken from an individual natural femur. Alternatively, it can also be an average shape determined for a collection of cadaveric knees. It can also be an average shape determined from a collection of MRI scans, either normal knees, or knees with some degeneration as seen in osteoarthritis. The averaging method can either be by a scaling process followed by the definition of numerous sagittal slices and then averaging the slices, from which a new composite three-dimensional shape is made. It can also use a surfacing software which places a mean surface through a point cloud in space, the points determined directly from digitizing cadaveric knees, or determining points from MRI sections, where the initial step is to scale and position the point clouds.

The outer femoral bearing surface is the same as the articular cartilage but includes the intercondylar areas 8, 11, 12, and 22, which are smoothly continuous with the condylar bearing surfaces 9, 10, 20, 21. The superior of the patella flange 3 can be extended from the cartilage bearing surface by approximately 5 mm to increase the contact with the anatomic patella or a resurfaced patella. The femoral component includes the lateral prominence 5 and the medial prominence 6 of the patella groove 4. The patella groove 7 continues smoothly into the intercondylar area 8. This area is continued into the posterior 23, and is blended at each side with the posterior lateral 21 and posterior medial 20 femoral condyles. The inclusion of the intercondylar area into the bearing surfaces is that the central part of the tibial component will interface during function, thus providing a larger surface area for motion guiding and stability. The entire periphery of the femoral component 2 is ideally continuous with the distal femur 1. This could be achieved by using a customized approach for each femur. However it is recognized that for a system of total knees with a finite number of sizes, for a given femur, even the closest size of component will have some discrepancy with the bone to which it is fitted. It might therefore be an advantage if the height of the posterior femoral condyles 24, 25 is made a few millimeters higher than the average size of femur.

FIGS. 3 and 4 show the shape of the femoral component 2 and bone cuts which are required for fitting. The cuts shown are typical of standard faceted cuts used for fitting the femoral components of most of today's total knee systems. The facets consist of the postero-lateral 30, postero-medial 31, distal lateral 32, distal medial 33 and anterior 34. There are usually smaller additional facets at approximately 45 degrees to the above cuts 35, 36, 37, and 38. Of particular interest are the bone cuts used for the intercondylar area 39. These are shown as rectangular cuts which preserve sufficient wall thickness of the femoral component 2. The resulting shaped housing is of relatively small dimensions requiring only a small amount of bone resection. In a sagittal view the anterior housing face makes an angle of approximately 60 degrees to the horizontal. In an alternative embodiment, the proximal surface of intercondylar area 39 may be formed as a smooth surface at least partially conformal with the distal surface of intercondylar area 39 thereby providing a constant wall thickness. The wall thickness in an exemplary embodiment is approximately 2 mm. This configuration has the advantage of requiring the removal of less bone than the rectangular cut embodiment. In addition, the absence of rectangular corners minimizes the possibility of high stress areas. The required bone resection may be cut with a box chisel or curved rasp.

FIG. 5 shows a lateral view of the femoral component 2 with the positions of three sections. The section at 0 degrees flexion 43 is in a vertical frontal plane. The section at 45 degrees flexion 44 is halfway between a vertical frontal plane and a transverse horizontal plane. The section at 90 degrees flexion 45 is on a transverse horizontal plane. The sectional profiles of the lateral 41 and medial 40 condyles, differ and are based on the known anatomic shapes. This difference is important in terms of preserving the correct lengths of the lateral and medial collateral ligaments during the entire range of flexion-extension. The prominence of the patella flange on the lateral side 42 is a normal feature of the anatomic knee, which maintains the patella in the trochlea groove without lateral dislocation. The amount of prominence varies between patients, in particular between males and females. The prominence is generally less with females than males. In any case, the prominence can be reduced, in order to reduce the tensions in the anterior soft tissue structures, thereby facilitating a high flexion range.

Figure 6:
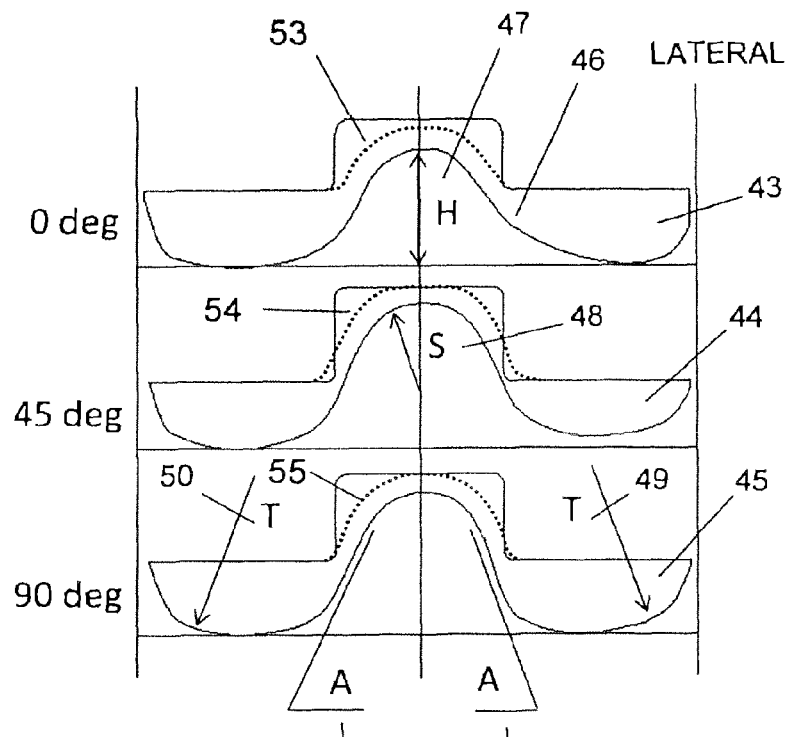
FIG. 6 shows 3 frontal sections through the femoral component at angles of 0 degrees, 45 degrees and 90 degrees from the distal end.

FIG. 6 shows the sectional views 43, 44, 45 together with preferred dimensions. The sections are generally similar in shape. The height of the housing H 47 is 16 mm at 0 degrees flexion and 19 mm at 45 and 90 degrees flexion. Preferred values are within 2 mm of these values. The radius of the dome S 48 is 8 mm in all sections, with a preferred value within 2 mm. The frontal radius of the lateral 49 and medial 50 femoral condyles is 22 mm with a preferred value within 2 mm. The angle of the sides of the housing A 51, 52 is 70 degrees to the horizontal within a preferred value within 5 degrees. The exception is the angle at 0 degrees flexion which is closer to 60 degrees in order to provide normal tracking of a retained anatomic patella. While the frontal shape of the housing seen on the abovementioned coronal sections can be rectangular for convenience of bone preparation, for preservation of more bone, the sections can be rounded 53, 54, 55 so as to provide a uniform wall thickness of approximately 2 mm. Rounding of the corners of the coronal sections of the femoral component and corresponding bone resection can also reduce undesirable stress concentrations.

A baseline tibial surface may be generated from the mating femoral bearing surface as an envelope of the composite of multiple distal femoral bearing surfaces positioned, with respect to said tibial component, throughout the full range of flexure angles and axial rotation angles. The full range of flexion-extension typically extends from approximately 150 degrees flexion to −6 degrees extension while the full range of axial rotation angles is typically 10 to 20 degrees. The baseline tibial surface thus generated will exhibit complete conformity between the two surfaces in full extension, full flexion, and at the sides. While this will maximize contact area and minimize contact stresses, it is undesirable for three reasons. Firstly, it does not allow for any positional errors in placing the components at surgery. Secondly, any small manufacturing errors could result in contacts at the edges of the plastic tibial component. Thirdly in function, shear forces will cause the femoral component to contact the edges of the tibial surface, possibly resulting in deformity. Hence some lack of conformity between the femoral and tibial surfaces is desirable. For convenience this is preferably effected on the tibial surface. Starting with the generated baseline tibial surface, a proximal tibial bearing surface may be generated by modifying the baseline tibial surface. One such modification is to 'flatten' the tibial surface mathematically. FIGS. 7, 8, 9, 10 show this visually, where FIGS. 7 and 9 is a tibial component 70 comprising the baseline tibial surfaces 69 generated directly by, and conformal with, the femoral component, while FIGS. 8 and 10 show the 'flattened surfaces', 71 and 72, of the proximal tibial bearing surface. This flattening is achieved by defining a transverse reference plane 100 containing the lowest point on the tibial bearing surfaces, and then scaling the height, above the transverse reference plane 100, of each point on the tibial bearing surface by a scaling constant having a value less than 1 (one). In the above figures, the exemplary scaling constant is 0.7, which is chosen for visualization purposes. The preferred value of the scaling constant for functional purposes is one that will allow approximately +/−1 mm medial-lateral laxity. In some embodiments the constant has been empirically found to be in the range of 0.8-0.9.

Figure 11:
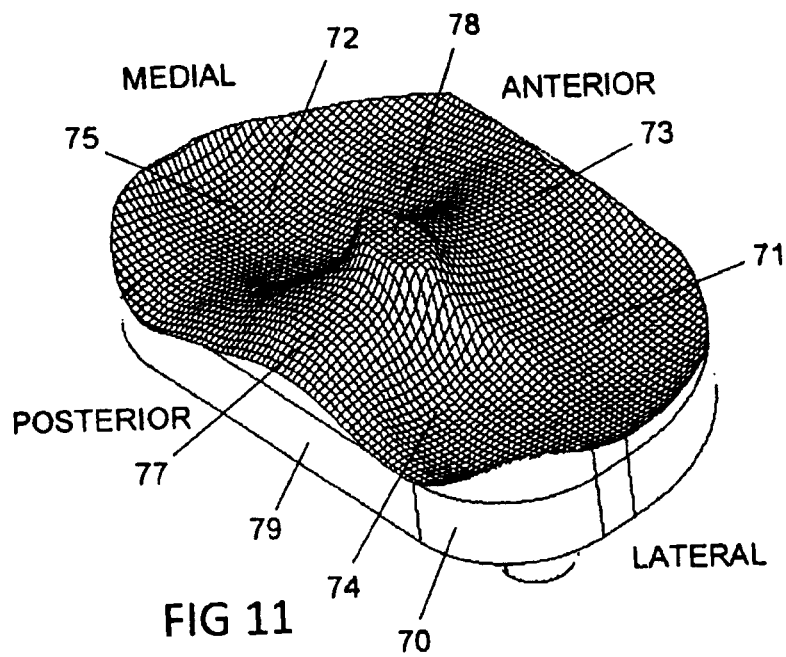
FIG. 11 is a posterior-lateral view of the tibial component.
Figure 12:
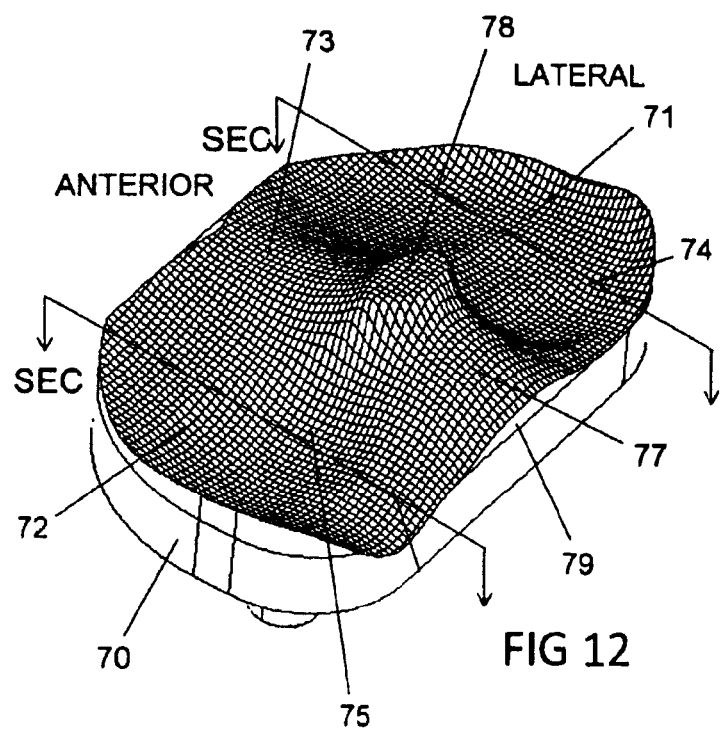
FIG. 12 is a posterior-medial view of the tibial component.
Figure 12A:
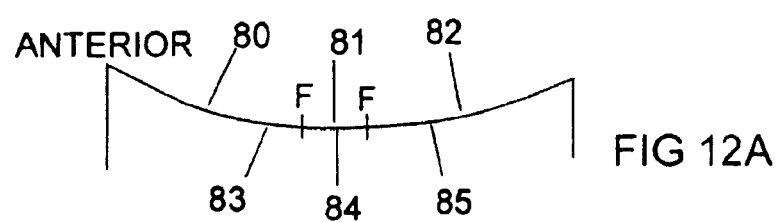
FIG. 12A is a sagittal section view of a tibial surface taken from the tibial component shown in FIG. 12.

FIGS. 11 and 12 are two views of the tibial component 70 with a scaling constant of 0.9. The central anterior surface 73 is in contact with the femoral component in approximately 3-6 degrees of hyperextension, which will allow for variations between individuals, but also as a soft stop to prevent excessive hyperextension, as the femoral component rocks upwards as it extends further. The lateral bearing surface 71 is generally flat in an anterior-posterior direction, or with a shallow dishing of approximately 80-100 mm radius seen in the sagittal plane. This shallow region extends close to the posterior 74. The medial bearing surface 72 is dished in the central region allowing only 2-4 mm of anterior-posterior displacement of the femur on the tibia. This dished region is shown as 75. The posterior central region 77 makes contact with the femur in high flexion after approximately 90 degrees flexion. This region enhances the contact area providing a continuous contact with the tibial surface extending from the lateral to the medial condyle. As shown, the tibial component has no provision for a notch in the proximal tibia at the location of the posterior cruciate ligament. Alternatively, a PCL notch can be provided in region 79. The surface of central hump 78 (which has been truncated), is generated by conformal contact with the corresponding surface of the articulating femoral component. The slopes leading into the hump 78 are in smooth continuity with the surrounding bearing surfaces 71, 72, 73, 77. This allows for smoothness of internal-external rotation of the femoral surface on the tibial surface. A refinement of the sagittal sections (SEC) of the tibial surface is shown schematically in FIG. 12A. It has been described that the tibial surface is generated from a multiplicity of positions of the femoral component and that part of the generation includes posterior displacements of the femoral component on the tibia so as to produce flat regions FF in the centers of the lateral and medial plateaus. The resulting section comprises an anterior circular segment having a first radius 80, a flat center segment 81, and a posterior circular segment having a second radius 82. This can be refined (shown dotted in FIG. 12A) wherein the resulting section comprises an anterior circular segment having a first radius 83, directly meeting a posterior circular segment having a second radius 85, at location 84.

Figure 13:
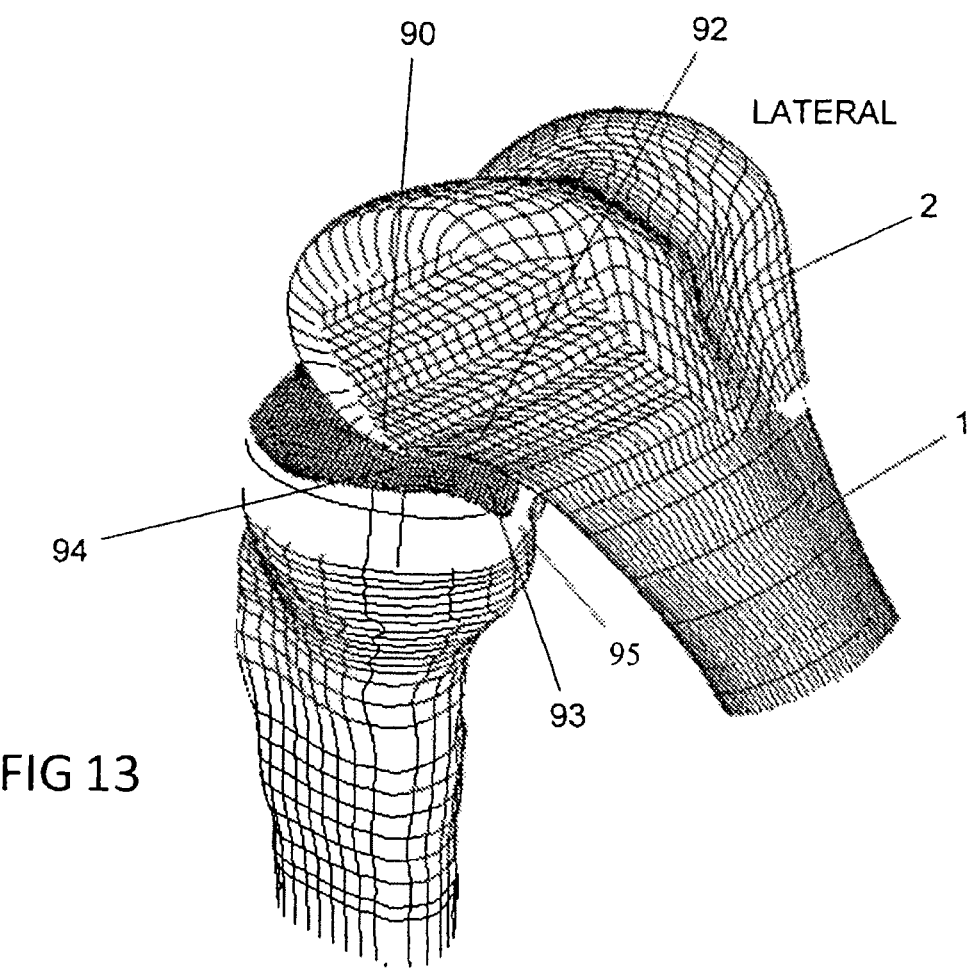
FIG. 13 is a posterior-medial view of the femoral and tibial components mounted on their respective bones at 150 degrees flexion, showing the posterior depression on the medial tibial bearing surface, matching the posterior-medial femoral component and femur.

FIG. 13 shows the femur 1 and femoral component 2 at 150 degrees of flexion. The femoral-tibial contact location 94 is close to the center of the tibia or a few millimeters posterior, as is the case for the anatomic knee. In the latter such high flexion is achieved by the posterior femur impacting the posterior horn of the medial meniscus, and levering over it. For a total knee this is not possible because of the rigidity of the materials. Hence one solution, shown in FIG. 13, is to relieve the posterior of the tibial surface 93. This relieved tibial surface 95 is defined by taking the continuous surface of the posterior femoral condyle 90 and the femur 92, and subtracting the combined surface from the tibial component 93. This subtraction can usually be carried out as shown, or for a femoral component where the posterior medial femoral condyle is extended superiorly. Note the subtraction is best carried out with the femur in a range of displaced and rotated orientations to include all functional positions.

In embodiments presented herein, the replacement of the function of the cruciates and the menisci of the anatomic knee, may be improved, so as to cause more normal medial pivot action, lateral femoral rollback in flexion, and roll-forward in extension. The embodiments herein presented incorporate features, in addition to those of the previous design, comprising retention of the intercondylar tibial eminences 78 and matching intercondylar femoral surfaces 22. These features provide the required medial-lateral constraint and also help to generate some of the anatomic motion characteristics described above. A further advantage of using anatomic surfaces, especially on the femur, is that anatomic patella tracking will occur, important for quadriceps mechanics.

The addition of the Intercondylar Guiding Surfaces 22, provides a more definitive guidance to the pivotal motion. The Intercondylar Guiding Surfaces 22 cause the femur to displace posteriorly in flexion, but because of greater medial than lateral tibial dishing, most of the posterior displacement will occur on the lateral side, more closely resembling normal anatomic motion. The Intercondylar Guiding Surface 22 is designed to be in contact with tibial eminence 78 throughout flexion, providing a smooth motion and continuous guidance to the motion. The surfaces are rounded and always have contacts over discrete areas, rather than being small 'point contacts' at corners or edges. The Intercondylar Guiding Surfaces 22 may be configured to minimize the required bone resection.

In embodiments, normal medial pivot action may be enhanced by making the antero-medial femoral surface steeper. Femoral surface steepness may be increased by removal of material from the anterior portion of the medial condyle. This steeper medial condylar anterior surface when articulated with a correspondingly steeper anterior tibial surface, produces the desired anterior-posterior displacement stabilization.

STATEMENT REGARDING PREFERRED EMBODIMENTS

While the invention has been described with respect to preferred embodiments, those skilled in the art will readily appreciate that various changes and/or modifications can be made to the invention without departing from the spirit or scope of the invention as defined by the appended claims. All documents cited herein are incorporated by reference herein where appropriate for teachings of additional or alternative details, features and/or technical background.

What is claimed:

1. A knee replacement implant comprising:
a tibial component comprising a proximal tibial bearing surface; and
a femoral component comprising an outer femoral bearing surface, said outer femoral bearing surface configured to engage said proximal tibial bearing surface and rotate relative to said proximal tibial bearing surface through a full range of flexure angles;
wherein said outer femoral bearing surface comprises a medial condylar region, a lateral condylar region, and an intercondylar region;
wherein said proximal tibial bearing surface is structured such that said proximal tibial bearing surface is formed from a baseline tibial bearing surface when each point of said proximal tibial bearing surface is scaled by a constant scaling factor greater than one relative to a transverse reference plane, wherein said transverse reference plane includes a most distal point of said proximal tibial bearing surface, and said baseline tibial bearing surface is defined as a composite of multiple outer femoral bearing surfaces positioned, with respect to said tibial component, throughout said range of flexure angles including in full extension and full flexion.

2. The knee replacement implant of claim 1, wherein the proximal tibial bearing surface comprises a lateral bearing surface that has a substantially flat region in a center of a sagittal section.

3. The knee replacement implant of claim 1, wherein the proximal tibial bearing surface comprises a medial bearing surface with dishing in a central region that allows for only 2-4 mm of anterior-posterior displacement between the femoral component and the tibial component.

4. The knee replacement implant of claim 1, wherein the proximal tibial bearing surface comprises a posterior central region that contacts the femoral component at flexion after 90 degrees, and wherein the femoral component and the tibial component are in continuous contact extending from the lateral condylar region to the medial condylar region at flexion after 90 degrees.

5. The knee replacement implant of claim 1, wherein the proximal tibial bearing surface comprises an anterior central region that contacts the femoral component at 3-6 degrees of hyperextension.

6. The knee replacement implant of claim 1, wherein the proximal tibial bearing surface of the tibial component has a relieved posterior surface that provides a femoral-tibial contact location at a center of the tibial component when the femoral component is at an upper flexion limit of the full range of flexure angles.

7. The knee replacement implant, in accordance with claim 1, wherein:
each of said medial condylar, lateral condylar and intercondylar regions defined by a plurality of coronal cross-sections, each coronal cross-section corresponding to one of a succession of angles of flexure of said femoral component, wherein each of said plurality of coronal cross-sections comprise a convex medial condylar segment, tangentially and smoothly transitioning into a concave intercondylar segment, tangentially and smoothly transitioning into a convex lateral condylar segment, each of said intercondylar segments in the plurality of coronal cross-sections having the same intercondylar radius, each of said intercondylar segments in the plurality of coronal cross-sections having an intercondylar outer surface and an intercondylar proximal surface, a thickness between said intercondylar outer surface and said intercondylar proximal surface is uniform in each of the plurality of coronal cross-sections.

8. The knee replacement implant, in accordance with claim 7, wherein said thickness is 2 mm to 4 mm in each of the plurality of coronal cross-sections.

9. The knee replacement implant, in accordance with claim 7, wherein said proximal tibial bearing surface comprises a posterior-medial portion that is in conformity with said outer femoral bearing surface and adjacent bone at a maximum angle of flexure.

10. The knee replacement implant, in accordance with claim 7, wherein an intercondylar housing height of said coronal cross-sections is 16 mm at 0 degrees flexion and 19 mm at 45 degrees and 90 degrees flexion.

11. The knee replacement implant, in accordance with claim 7, wherein an intercondylar sidewall angle in each of the plurality of coronal cross-sections is between 55 and 75 degrees relative to said transverse reference plane.

12. The knee replacement implant, in accordance with claim 7, wherein said intercondylar radius in each of the plurality of coronal cross-sections is between 6 mm and 10 mm.

13. The knee replacement implant, in accordance with claim 1, wherein said proximal tibial bearing surface comprises greater dishing in the central region of a proximal-medial portion of said proximal tibial bearing surface compared to dishing in a central region of a proximal-lateral portion of said proximal tibial bearing surface.

* * * * *